(12) United States Patent
Han et al.

(10) Patent No.: US 10,919,791 B2
(45) Date of Patent: Feb. 16, 2021

(54) INTELLIGENT IDENTIFICATION METHOD OF SLUDGE BULKING BASED ON TYPE-2 FUZZY NEURAL NETWORK

(71) Applicant: BEIJING UNIVERSITY OF TECHNOLOGY, Beijing (CN)

(72) Inventors: Honggui Han, Beijing (CN); Hongxu Liu, Beijing (CN); Jiaming Li, Beijing (CN); Junfei Qiao, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 294 days.

(21) Appl. No.: 16/143,409

(22) Filed: Sep. 26, 2018

(65) Prior Publication Data
US 2020/0024168 A1    Jan. 23, 2020

(30) Foreign Application Priority Data

Jul. 18, 2018  (CN) .......................... 201810790763.9

(51) Int. Cl.
*C02F 3/00* (2006.01)
*G06F 30/20* (2020.01)
*C02F 3/12* (2006.01)
*G01N 33/18* (2006.01)
(Continued)

(52) U.S. Cl.
CPC .............. *C02F 3/006* (2013.01); *C02F 3/12* (2013.01); *G01N 33/18* (2013.01); *G06F 30/20* (2020.01); *G06N 3/0436* (2013.01); *C02F 2209/02* (2013.01); *C02F 2209/06* (2013.01); *C02F 2209/16* (2013.01); *C02F 2209/22* (2013.01); *G06F 2111/10* (2020.01)

(58) Field of Classification Search
None
See application file for complete search history.

(56) References Cited

U.S. PATENT DOCUMENTS

| | | | |
|---|---|---|---|
| 2017/0185892 A1* | 6/2017 | Han | G06N 3/082 |
| 2018/0029900 A1* | 2/2018 | Han | G06N 3/0481 |

* cited by examiner

*Primary Examiner* — Roy Y Yi
(74) *Attorney, Agent, or Firm* — J.C. Patents

(57) ABSTRACT

An intelligent identification method of sludge bulking based on type-2 fuzzy-neural-network belongs to the field of intelligent detection technology. The sludge volume index (SVI) in wastewater treatment plant is an important index to measure the sludge bulking of activated sludge process. However, poor production conditions and serious random interference in sewage treatment process are characterized by strong coupling, large time-varying and serious hysteresis, which makes the detection of SVI concentration of sludge volume index extremely difficult. At the same time, there are many types of sludge bulking faults, which are difficult to identify effectively. Due to the sludge volume index (SVI) is unable to online monitoring and the fault type of sludge bulking is difficult to determined, the invention develop soft-computing model based on type-2 fuzzy-neural-network to complete the real-time detection of sludge volume index (SVI). Combined with the target-related identification algorithm, the fault type of sludge bulking is determined. Results show that the intelligent identification method can quickly obtain the sludge volume index (SVI), accurate identification fault type of sludge bulking, improve the quality and ensure the safety operation of the wastewater treatment process.

1 Claim, 4 Drawing Sheets

(51) Int. Cl.
*G06N 3/04* (2006.01)
*G06F 111/10* (2020.01)

INTELLIGENT IDENTIFICATION METHOD OF SLUDGE BULKING BASED ON TYPE-2 FUZZY NEURAL NETWORK

CROSS-REFERENCE TO RELATED APPLICATION

This application claims the priority benefit of Chinese application serial no. 201810790763.9, filed Jul. 18, 2018. All disclosure of the China application is incorporated herein by reference.

TECHNOLOGY AREA

Based on the running characteristics of wastewater treatment process and using type-2 fuzzy neural network, the invention design an intelligent identification method to realize the real-time measurement about index SVI of sludge bulking in wastewater treatment process and the identification for fault categories of sludge bulking, where the concentration of sludge volume index SVI in wastewater treatment plant is the performance index of measuring the coagulation sedimentation and thickening properties of activated sludge. The prediction of sludge volume index SVI and identification of fault category of sludge bulking have a great significance for realizing the monitoring and controlling in wastewater treatment process. It have great important influence for energy saving and safety operation to apply intelligent recognition method in wastewater treatment system. Moreover, the above methods belonging to the control field and water treatment field simultaneously, is the important branch for the field of advanced manufacturing technology. Therefore, the intelligent recognition of the sludge bulking is of great significance in the wastewater treatment system.

TECHNOLOGY BACKGROUND

During the development in past hundred years, the wastewater treatment technology of activated sludge process has become the mainstream of urban wastewater treatment technology in the worldwide. However, in China, the present wastewater treatment plant have the drawback that backward wastewater treatment equipment, low-end automation level and incomplete control system, which lead to the high frequency occurrence of sludge bulking. Sludge bulking can lead to loose sludge structure, increasing sludge volume and reduction of sludge sedimentation velocity and then, there is difficult for solid settlement separation which affect water quality and damage the normal and stable operation of activated sludge system in the wastewater treatment process. Therefore, it is of great significance to analyze the phenomenon of sludge bulking and study the diagnosis method of sludge bulking to improve the efficiency and ensure the normal operation of working condition for wastewater treatment process.

At present, many study for identifying sludge bulking phenomenon have development, but the implementation effect is not optimistic. On the one hand, due to the complex mechanism properties of sludge bulking, mechanism model based sludge bulking diagnosis method cannot cover all the growth mechanism of microorganism to meets the stability and the accuracy simultaneously. Moreover, mechanism model based sludge bulking diagnosis method judge sludge bulking by measuring the length, abundance and others morphological characteristics of the microorganism what have the characteristics of complex operation and strong time-delay and is difficult to be applied in the wastewater treatment process. On the other hand, the dynamic nonlinear of wastewater treatment process make traditional sludge bulking prediction model is difficult to adapt the working condition with strong dynamic change and identify the fault type of sludge bulking accurately. Based on the negative influence of the sludge bulking, design a sludge bulking diagnostic method which character real-time dynamic tracking, accurate and stable have important theoretical significance and application value for monitoring wastewater treatment process running online, stabilizing the wastewater treatment process, preventing the sludge bulking phenomenon, improving the water quality and increasing the efficiency of wastewater treatment.

The invention proposed a type-2 fuzzy neural network based intelligent diagnosis method about sludge bulking. The type-2 fuzzy neural network model and parameter optimization algorithm can improve the prediction performance of the network effectively and then, the fault type identification of sludge bulking is realized by target correlation recognition algorithm. The above intelligent identification method can realize the real-time detection of sludge volume index SVI and identification of fault type for sludge bulking. Moreover, the intelligent identification method also reduce the measurement cost, increase the identification accuracy, provides a fast and efficient identification mean and improve the benefit of the wastewater treatment plant.

SUMMARY OF THE PATENT

The invention proposed a type-2 fuzzy neural network based sludge bulking intelligent diagnosis method. First, the method analyze the wastewater treatment process and select a group of auxiliary variable which is closely related to the sludge volume index SVI and easily measured. Then, type-2 fuzzy neural network is used for measuring the sludge volume index SVI online. In the end, the target correlation recognition algorithm is applied for identifying the fault type of sludge bulking. The method solves the problem about long measurement cycle of sludge volume index SVI and identify difficulty of sludge bulking category.

The invention includes the following steps:

(1) Determine the input and output variables of sludge volume index (SVI): in the activated sludge wastewater treatment process, the input variables of SVI soft-computing model include: dissolved oxygen (DO) concentration, total nitrogen (TN) concentration, organic load rate (F/M), pH, T. The output value of soft-computing model is the SVI values. The sludge bulking contains the following fault types: low DO concentration, nutrient deficit, low sludge loading, low pH, and low temperature;

(2) SVI soft-computing model: establish SVI soft-computing model based on type-2 fuzzy-neural-network, the structure of type-2 fuzzy-neural-network contains five layers: input layer, membership function layer, firing layer, consequent layer and output layer, the network is 5-M-L-2-1, including 5 neurons in input layer, M neurons in membership function layer, L neurons in firing layer, 2 neurons in consequent layer and 1 neurons in output layer, M and L are the integers larger than 2; connecting weights between input layer and membership function layer are assigned 1; the number of the training sample is N, the input of type-2 fuzzy-neural-network is $x(t)=[x_1(t), x_2(t), x_3(t), x_4(t), x_5(t)]$ at time t, $x_1(t)$ represents the DO concentration at time t; $x_2(t)$ represents the TN concentration at time t, $x_3(t)$ represents the organic load rate (F/M) value at time t, $x_4(t)$ represents the pH value at time t, and $x_5(t)$ represents the T value at time t, the output of type-2 fuzzy-neural-network is $y_d(t)$ and the actual output is y(t); type-2 fuzzy-neural-network includes:

① input layer: there are 5 neurons in this layer, the output is:

$$o_i(t)=x_i(t) \quad (1)$$

where $o_i(t)$ is the ith output value at time t, i=1, 2, . . . , 5,

② membership function layer: there are M neurons in membership function layer, the output is:

$$\tau_m^i(t) = N(c_m^i(t), \sigma_m^i(t); o_i(t)) = \exp\left\{-\frac{1}{2}\left(\frac{o_i(t) - c_m^i(t)}{\sigma_m^i(t)}\right)^2\right\}, \quad (2)$$

$$i = 1, 2, \ldots, 5; m = 1, 2, \ldots, M,$$

$$c_m^i(t) \in [\underline{c}_m^i(t), \overline{c}_m^i(t)], \quad (3)$$

where $\tau_m^i(t)$ is the mth membership function with the ith input at time t, N represents the membership function, $c_m^i(t)$ is the uncertain center of the mth membership function neuron with the ith input at time t, $\underline{c}_m^i(t)$ is the lower center value of the mth membership function neuron with the ith input at time t, $\overline{c}_m^i(t)$ is the upper center value of the mth membership function neuron with the ith input at time t (where the initial lower center value and initial upper center value of the mth membership function neuron with the ith input i.e., $\underline{c}_m^i(0)$ and $\overline{c}_m^i(0)$ is obtained by that random initial center of the mth membership function neuron with the ith input $c_m^i(0)$ add and subtract a constant), $\sigma_m^i(t)$ is the standard deviation of the mth membership function neuron with the ith input at time t, the bounded internal of $\tau_m^i(t)$ is $[\underline{\tau}_m^i(t), \overline{\tau}_m^i(t)]$ $$\underline{\tau}_m^i(o_i(t)) = \begin{cases} N(\overline{c}_m^i(t), \sigma_m^i(t); o_i(t)), & o_i(t) \leq (\underline{c}_m^i(t) + \overline{c}_m^i(t))/2 \\ N(\underline{c}_m^i(t), \sigma_m^i(t); o_i(t)), & o_i(t) > (\underline{c}_m^i(t) + \overline{c}_m^i(t))/2 \end{cases}, \quad (4)$$

$$\overline{\tau}_m^i(o_i(t)) = \begin{cases} N(\underline{c}_m^i(t), \sigma_m^i(t); o_i(t)), & o_i(t) \leq \underline{c}_m^i(t) \\ 1, & \underline{c}_m^i(t) < o_i(t) < \overline{c}_m^i(t), \\ N(\overline{c}_m^i(t), \sigma_m^i(t); o_i(t)), & o_i(t) > \overline{c}_m^i(t) \end{cases} \quad (5)$$

where $\underline{\tau}_m^i(t)$ and $\overline{\tau}_m^i(t)$ are the lower value and upper value of the mth membership function neuron with the ith input at time t, respectively, $0 < \underline{\tau}_m^i(t) \leq \overline{\tau}_m^i(t) \leq 1$, ③ firing layer: there are L neurons in this layer, and the output values are:

$$F_l(t) = [\underline{f}_l(t), \overline{f}_l(t)], \underline{f}_l(t) = \prod_{i=1}^{5} \underline{\tau}_m^i(t), \overline{f}_l(t) = \prod_{i=1}^{5} \overline{\tau}_m^i(t), \quad (6)$$

$$l = 1, 2, \ldots, L,$$

where $F_l(t)$ is the firing strength of the lth firing neuron, $\underline{f}_l(t)$ and $\overline{f}_l(t)$ are the lower firing strength and upper firing strength of the lth firing neuron, respectively, $0 < \underline{f}_l(t) \leq \overline{f}_l(t) \leq 1$, ④ consequent layer: this layer contains two consequent neurons, the output values are $$\underline{y}(t) = \frac{\sum_{l=1}^{L} \underline{f}_l(t)a_l(t)}{\sum_{l=1}^{L} \underline{f}_l(t)}, \overline{y}(t) = \frac{\sum_{l=1}^{L} \overline{f}_l(t)a_l(t)}{\sum_{l=1}^{L} \overline{f}_l(t)}, \quad (7)$$

$$a_l(t) = \sum_{i=1}^{5} \theta_l^i(t)x_i(t),$$

where $\underline{y}(t)$ and $\overline{y}(t)$ are the low and up output values of the consequent neurons, $a_l(t)$ is weight of the lth firing neuron, $\theta_l^i(t)$ is the weight coefficient of the lth firing neuron with the ith input at time t, ⑤ output layer: the output value is:

$$y(t)=\eta(t)\underline{y}(t)+(1-\eta(t))\overline{y}(t) \quad (8)$$

where η(t) and y(t) are the proportion of the low output and the output value of type-2 fuzzy-neural-network, the error of type-2 fuzzy-neural-network is:

$$E(t) = \frac{1}{N} \sum_{t=1}^{N} (y_d(t) - y(t))^2 \quad (9)$$

where $y_d(t)$ is the output of type-2 fuzzy-neural-network and the actual output is expressed as y(t);

(3) train type-2 fuzzy-neural-network

① give the type-2 fuzzy-neural-network, the initial number of firing layer neurons is M, M>2 is a positive integer; the input of type-2 fuzzy-neural-network is x(1), x(2), . . . , x(t), . . . , x(N), correspondingly, the output is $y_d(1)$, $y_d(2)$, . . . , $y_d(t)$, . . . , $y_d(N)$, expected error value is set to $E_d$, $E_d \in (0, 0.01)$, ② set the learning step s=1;

③ t=s; according to Eqs. (1)-(7), calculate the output of type-2 fuzzy-neural-network, exploiting adaptive second-order algorithm:

$$\psi(t+1)=\psi(t)+(H(t)+\lambda(t)I)^{-1}v(t) \quad (10)$$

where $\psi(t)=[\underline{c}_m^i(t), \overline{c}_m^i(t), \sigma_m^i(t), \eta(t), w_m^i(t)]$ is the parameter matrix of type-2 fuzzy-neural-network at time t, $\underline{c}_m^i(t)$ is the lower center value of the mth membership function neuron with the ith input at time t, $\overline{c}_m^i(t)$ is the upper center value of the membership function neuron with the ith input at time t, $\sigma_m^i(t)$ is the standard deviation of the mth membership function neuron with the ith input at time t, η(t) is the proportion of the lower output, $\theta_l^i(t)$ is the weight coefficient of the lth firing neuron with the ith input at time t, H(t) is the quasi Hessian matrix, v(t) is gradient vector, I is the identity matrix and λ(t) is the adaptive learning rate defined as:

$$\lambda(t)=\gamma|E(t)|+(1-\gamma)\|v(t)\| \quad (11)$$

where $\gamma \in (0, 1)$, the expression of H(t) and v(t) are defined as:

$$H(t)=J^T(t)J(t) \quad (12)$$

$$v(t)=J^T(t)E(t) \quad (13)$$

where the Jacobian vector J(t) is calculated as:

$$J(t) = \left[\frac{\partial e(t)}{\partial \underline{c}_m^i(t)}, \frac{\partial e(t)}{\partial \overline{c}_m^i(t)}, \frac{\partial e(t)}{\partial \sigma_m^i(t)}, \frac{\partial e(t)}{\partial \eta(t)}, \frac{\partial e(t)}{\partial \theta_m^i(t)}\right] \quad (14)$$

④ according to Eq. (9), calculate the performance of type-2 fuzzy-neural-network, if $E(t) \geq E_d$, go to step ③; if $E(t) < E_d$, stop the training process;

(4) the target-related identification algorithm is used to determine the fault type of sludge bulking, which is specifically as follows:

① the test samples is used as the input of the type-2 fuzzy-neural-network, and the sludge volume index (SVI) is calculated;

② if SVI≤150, it is determined that there is no sludge bulking during the wastewater treatment process;

③ if SVI>150, sludge bulking at the wastewater treatment operation was determined and regression coefficients of all variables were calculated:

$$b_i(t) = \frac{u_i(t)^T t_i(t)}{t_i(t)^T t_i(t)}, \quad (15)$$

where $b_i(t)$ is the regression coefficient of ith input at time t, $b(t)=[b_1(t), \ldots, b_i(t), \ldots, b_5(t)]$ is the regression coefficient vector, $u_i(t)$ is the ith score vector of the output vector at time t, $U(t)=[u_1(t), \ldots, u_i(t), \ldots, u_5(t)]$ is score matrix of the output vector at time t, $t_i(t)$ is the ith score vector of the input matrix at time t, $T(t)=[t_1(t), \ldots, t_i(t), \ldots, t_5(t)]$ is score matrix of the input matrix at time t, $u_i(t)$ and $t_i(t)$ are given as:

$$u_i(t) = \frac{y(t)q_i(t)}{q_i(t)^T q_i(t)}, \quad (16)$$

$$t_i(t) = \frac{X(t)w_i(t)}{w_i(t)^T w_i(t)}, \quad (17)$$

where $q_i(t)$ is the ith loading value of output vector at time t, $q(t) \in R^{1 \times 5}$ is the loading vector of output vector at time t, $y(t)=[y(t-K+1), y(t-K+2), \ldots, y(t)]^T$, $y(t)$ is the SVI value at time t, $X(t)=[x_1(t), \ldots, x_i(t), \ldots, x_5(t)]$ is the input matrix of type-2 fuzzy-neural-network, $x_i(t)=[x_i(t-K+1), x_i(t-K+2), \ldots, x_i(t)]^T$, $x_i(t)$ is the ith input variable at time t, $w_i(t)$ is the ith feature vector at time t, $W(t)=[w_1(t), \ldots, w_i(t), \ldots, w_5(t)]$ is the feature matrix of $X(t)^T y(t)$, the expressions of $q_i(t)$ and $W(t)$ are $$q_i(t)^T = \frac{t_i(t)^T y(t)}{t_i(t)^T t_i(t)}, \quad (18)$$

$$W(t)^T \Lambda(t) W(t) = E\{X(t)^T y(t) y(t)^T X(t)\}, \quad (19)$$

where $\Lambda(t)$ is the eigenvalue matrices of $X(t)^T y(t)$, The function E represents the eigenvector and eigenvalue of the matrix, the inner relative model of $y(t)$ and $X(t)$ can be expressed as:

$$\begin{cases} X(t) = T(t)P(t)^T + \Delta(t) = \sum_{i=1}^{5} t_i(t)p_i(t)^T + \Delta(t) \\ y(t) = U(t)q(t)^T + G(t) = \sum_{i=1}^{5} u_i(t)q_i(t)^T + G(t) \end{cases}, \quad (20)$$

where $\Delta(t) \in R^{K \times 5}$ is the residual matrix of $X(t)$, $\Delta(t)=[\delta_1(t), \ldots, \delta_i(t), \ldots, \delta_5(t)]$, where $\delta_i(t)$ present the residual vector of ith input. $G(t) \in R^{K \times 1}$ is the residual vector of $y(t)$;

④ when the regression coefficient of the input variable satisfies:

$$b_{max}(t) = \max\, b(t), \quad (21)$$

where $b_{max}(t)$ is the maximum regression coefficient of the input variables, and the corresponding fault type is the source of sludge bulking.

The Novelties of this Patent Contain:

(1) Aiming at the problem that sludge bulking is difficult to identify in current wastewater treatment process, the invention proposed a type-2 fuzzy neural network based intelligent identification method. First, extract five relevant variables which is related to the sludge volume index SVI according to the work report of real-world wastewater treatment plant: dissolved oxygen concentration DO, total nitrogen TN, load activated sludge, F/M power of hydrogen pH and temperature T and then, realize the prediction of sludge volume index SVI. The invention solves the problem that sludge volume index SVI is hard to measure online, avoid the application of complicated sensor and reduces the running cost (2) Based on target correlation identification method, the invention identify the category of sludge bulking through the contribution of variable to sludge bulking. The above method can not only measure the influence intensity of variable in the sludge bulking process, but also identify the fault category of the sludge bulking what solve the difficult identification of sludge bulking in the wastewater treatment process. Moreover, the target correlation identification method is used for identifying the fault category of sludge bulking online, what has the characteristics of high precision and the strong adaptability to environmental variation.

Attention: the invention adopts type-2 fuzzy neural network and the target correlation identification algorithm to establish the sludge bulking intelligent recognition method. The research that adopt type-2 fuzzy neural network and target correlation identification algorithm in this invention for intelligent identification of sludge bulking, should fall within the scope of the present invention

DETAILED DESCRIPTION OF THE INVENTION

Figure 1:
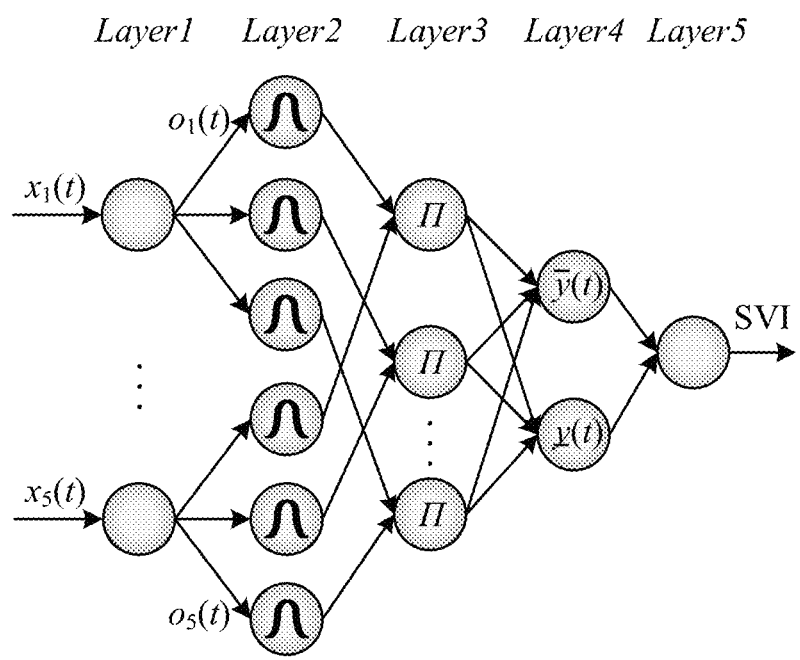
FIG. 1 is the initial structural topology diagram of the type-2 fuzzy neural network.

The invention select the characteristic variables to measure sludge volume index SVI as dissolved oxygen concentration DO, total nitrogen TN, load activated sludge F/M, power of hydrogen pH and temperature T, where pH no unit. The unit of temperature is Celsius. Others units are mg/l.

The experimental data come from the 2017 water quality data analysis report of a wastewater treatment plant. Where the actual testing data about dissolved oxygen concentration DO, total nitrogen TN, load activated sludge F/M, power of hydrogen pH and temperature T is selected for the experimental sample data. There are 1000 groups data are available after eliminate the abnormal, where 500 group used as training samples and the rest of 500 as test sample. The technical scheme and implementation steps as following.

An intelligent identification method for sludge bulking based on a type-2 fuzzy-neural-network comprise the following steps:

(1) Determine the input and output variables of sludge volume index (SVI): in the activated sludge wastewater treatment process, the input variables of SVI soft-computing model include: dissolved oxygen (DO) concentration, total nitrogen (TN) concentration, organic load rate (F/M), pH, T. The output value of soft-computing model is the SVI values. The sludge bulking contains the following fault types: low DO concentration, nutrient deficit, low sludge loading, low pH, and low temperature;

(2) SVI soft-computing model: establish SVI soft-computing model based on type-2 fuzzy-neural-network, the structure of type-2 fuzzy-neural-network contains five layers: input layer, membership function layer, firing layer, consequent layer and output layer, the network is 5-15-3-2-1, including 5 neurons in input layer, 15 neurons in membership function layer, 3 neurons in firing layer, 2 neurons in consequent layer and 1 neurons in output layer; connecting weights between input layer and membership function layer are assigned 1; the number of the training sample is N, the input of type-2 fuzzy-neural-network is $x(t)=[x_1(t), x_2(t), x_3(t), x_4(t), x_5(t)]$ at time t, $x_1(t)$ represents the DO concentration at time t; $x_2(t)$ represents the TN concentration at time t, $x_3(t)$ represents the organic load rate (F/M) value at time t, $x_4(t)$ represents the pH value at time t, and $x_5(t)$ represents the T value at time t, the output of type-2 fuzzy-neural-network is $y_d(t)$ and the actual output is $y(t)$; type-2 fuzzy-neural-network includes:

① input layer: there are 5 neurons in this layer, the output is:

$$o_i(t)=x_i(t) \quad (1)$$

where $o_i(t)$ is the ith output value at time t, i=1, 2, . . . , 5,

② membership function layer: there are M neurons in membership function layer, the output is:

$$\tau_m^i(t) = N(c_m^i(t), \sigma_m^i(t); o_i(t)) = \exp\left\{-\frac{1}{2}\left(\frac{o_i(t) - c_m^i(t)}{\sigma_m^i(t)}\right)^2\right\}, \quad (2)$$

$$i = 1, 2, \ldots, 5; m = 1, 2, \ldots, M,$$

$$c_m^i(t) \in [\underline{c}_m^i(t), \overline{c}_m^i(t)], \quad (3)$$

where $\tau_m^i(t)$ is the mth membership function with the ith input at time t, N represents the membership function, $c_m^i(t)$ is the uncertain center of the mth membership function neuron with the ith input at time t, $\underline{c}_m^i(t)$ is the lower center value of the mth membership function neuron with the ith input at time t, $\overline{c}_m^i(t)$ is the upper center value of the mth membership function neuron with the ith input at time t (where the initial lower center value and initial upper center value of the mth membership function neuron with the ith input i.e., $\underline{c}_m^i(0)$ and $\overline{c}_m^i(t)$ is obtained by that random initial center of the mth membership function neuron with the ith input $c_m^i(0)$ add and subtract a constant), $\sigma_m^i(t)$ is the standard deviation of the mth membership function neuron with the ith input at time t, the bounded internal of $\tau_m^i(t)$ is $[\underline{\tau}_m^i(t), \overline{\tau}_m^i(t)]$ $$\underline{\tau}_m^i(o_i(t)) = \begin{cases} N(\overline{c}_m^i(t), \sigma_m^i(t); o_i(t)), & o_i(t) \leq (\underline{c}_m^i(t) + \overline{c}_m^i(t))/2 \\ N(\underline{c}_m^i(t), \sigma_m^i(t); o_i(t)), & o_i(t) > (\underline{c}_m^i(t) + \overline{c}_m^i(t))/2 \end{cases}, \quad (4)$$

$$\overline{\tau}_m^i(o_i(t)) = \begin{cases} N(\underline{c}_m^i(t), \sigma_m^i(t); o_i(t)), & o_i(t) \leq \underline{c}_m^i(t) \\ 1, & \underline{c}_m^i(t) < o_i(t) < \overline{c}_m^i(t) \\ N(\overline{c}_m^i(t), \sigma_m^i(t); o_i(t)), & o_i(t) > \overline{c}_m^i(t) \end{cases} \quad (5)$$

where $\underline{\tau}_m^i(t)$ and $\overline{\tau}_m^i(t)$ are the lower value and upper value of the mth membership function neuron with the ith input at time t, respectively, $0<\underline{\tau}_m^i(t)\leq\overline{\tau}_m^i(t)\leq 1$, ③ firing layer: there are L neurons in this layer, and the output values are:

$$F_l(t) = [\underline{f}_l(t), \overline{f}_l(t)], \underline{f}_l(t) = \prod_{i=1}^{5} \underline{\tau}_m^i(t), \overline{f}_l(t) = \prod_{i=1}^{5} \overline{\tau}_m^i(t), \quad (6)$$

$$l = 1, 2, \ldots, L,$$

where $F_l(t)$ is the firing strength of the lth firing neuron, $\underline{f}_l(t)$ and $\overline{f}_l(t)$ are the lower firing strength and upper firing strength of the lth firing neuron, respectively, $0<\underline{f}_l(t)\leq\overline{f}_l(t)\leq 1$, ④ consequent layer: this layer contains two consequent neurons, the output values are $$\underline{y}(t) = \frac{\sum_{l=1}^{L} \underline{f}_l(t)a_l(t)}{\sum_{l=1}^{L} \underline{f}_l(t)}, \quad \overline{y}(t) = \frac{\sum_{l=1}^{L} \overline{f}_l(t)a_l(t)}{\sum_{l=1}^{L} \overline{f}_l(t)}, \quad (7)$$

$$a_l(t) = \sum_{i=1}^{5} \theta_l^i(t)x_i(t),$$

where $\underline{y}(t)$ and $\overline{y}(t)$ are the low and up output values of the consequent neurons, $a_l(t)$ is weight of the lth firing neuron, $\theta_l^i(t)$ is the weight coefficient of the lth firing neuron with the ith input at time t, ⑤ output layer: the output value is:

$$y(t)=\eta(t)\underline{y}(t)+(1-\eta(t))\overline{y}(t) \quad (8)$$

where $\eta(t)$ and $y(t)$ are the proportion of the low output and the output value of type-2 fuzzy-neural-network, the error of type-2 fuzzy-neural-network is:

$$E(t) = \frac{1}{N}\sum_{i=1}^{N}(y_d(t) - y(t))^2 \quad (9)$$

where $y_d(t)$ is the output of type-2 fuzzy-neural-network and the actual output is expressed as $y(t)$;

(3) train type-2 fuzzy-neural-network

① give the type-2 fuzzy-neural-network, the initial number of firing layer neurons is M, M>2 is a positive integer; the input of type-2 fuzzy-neural-network is $x(1), x(2), \ldots, x(t), \ldots, x(N)$, correspondingly, the output is $y_d(1), y_d(2), \ldots, y_d(t), \ldots, y_d(N)$, expected error value is set to $E_d$, $E_d \in (0, 0.01)$, ② set the learning step s=1;

③ t=s; according to Eqs. (1)-(7), calculate the output of type-2 fuzzy-neural-network, exploiting adaptive second-order algorithm:

$$\psi(t+1)=\psi(t)+(H(t)+\lambda(t)I)^{-1}v(t) \quad (10)$$

where $\psi(t)=[\underline{c}^i_m(t), \bar{c}^i_m(t), \sigma^i_m(t), \eta(t), w^i_m(t)]$ is the parameter matrix of type-2 fuzzy-neural-network at time t, $\underline{c}^i_m(t)$ is the lower center value of the mth membership function neuron with the ith input at time t, $\bar{c}^i_m(t)$ is the upper center value of the membership function neuron with the ith input at time t, $\sigma^i_m(t)$ is the standard deviation of the mth membership function neuron with the ith input at time t, $\eta(t)$ is the proportion of the lower output, $\theta^i_l(t)$ is the weight coefficient of the lth firing neuron with the ith input at time t, H(t) is the quasi Hessian matrix, v(t) is gradient vector, I is the identity matrix and $\lambda(t)$ is the adaptive learning rate defined as:

$$\lambda(t)=\gamma|E(t)|+(1-\gamma)\|v(t)\| \tag{11}$$

where $\gamma\in(0, 1)$, the expression of H(t) and v(t) are defined as:

$$H(t)=J^T(t)J(t) \tag{12}$$

$$v(t)=J^T(t)E(t) \tag{13}$$

where the Jacobian vector J(t) is calculated as:

$$J(t) = \left[\frac{\partial e(t)}{\partial \underline{c}^i_m(t)}, \frac{\partial e(t)}{\partial \bar{c}^i_m(t)}, \frac{\partial e(t)}{\partial \sigma^i_m(t)}, \frac{\partial e(t)}{\partial \eta(t)}, \frac{\partial e(t)}{\partial \theta^i_m(t)}\right] \tag{14}$$

Figure 2:
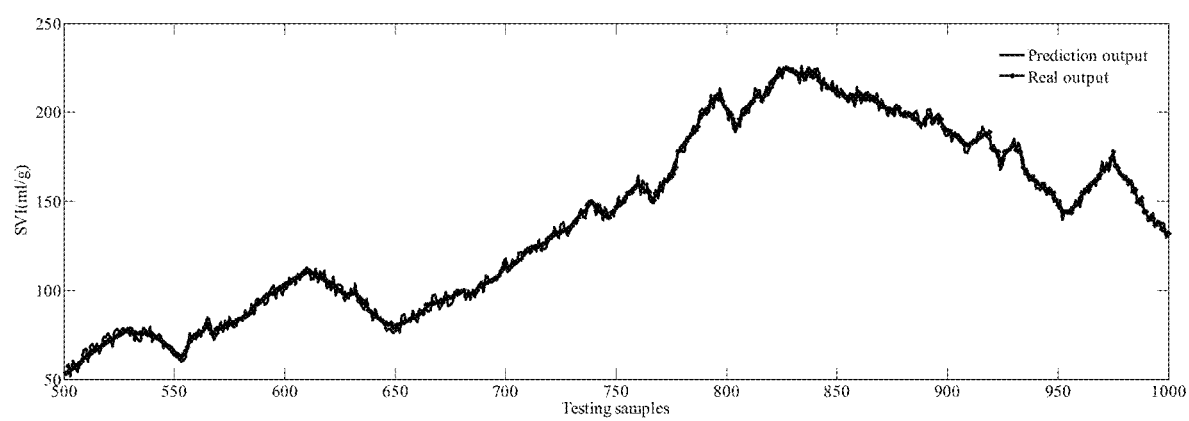
FIG. 2 is the SVI test result diagram of the sludge volume index, where the blue line is the desired output value of sludge volume index SVI, and the black line is the predicted value of type-2 fuzzy neural network.
Figure 3:
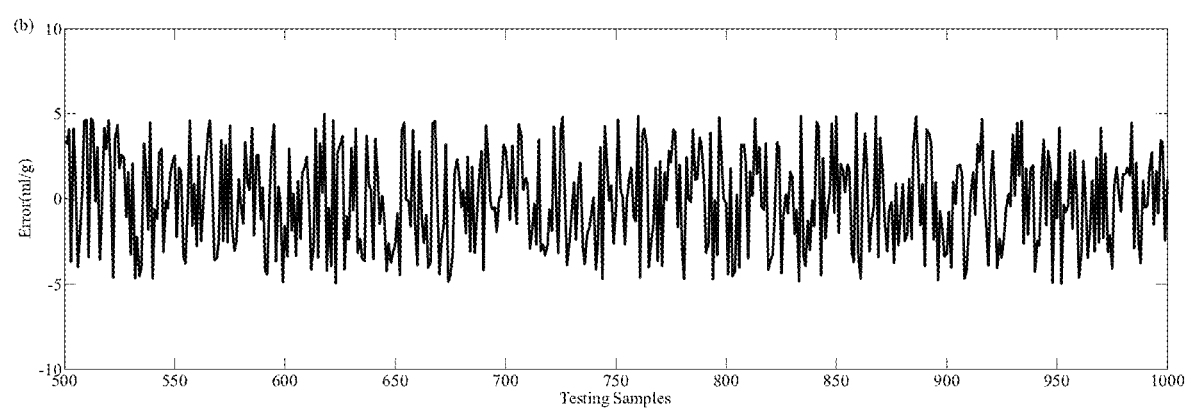
FIG. 3 is the SVI prediction error diagram of the sludge volume index.

④ according to Eq. (9), calculate the performance of type-2 fuzzy-neural-network, if $E(t)\geq E_d$, go to step ③; if $E(t)<E_d$, stop the training process;

The predicted results of sludge volume index SVI is shown in FIG. 2, the X axis: sample, the unit is a; Y axis: the test output of sludge volume index SVI, the unit is ml/g; the blue line is the predict output value of sludge volume index SVI; the black line is actual output values of sludge volume index SVI; The error between the predicted output and the actual output of sludge volume index (SVI) is shown in FIG. 3. The X axis: sample, the unit is a; Y axis: the test output of sludge volume index SVI, the unit is ml/g;

(4) The target-related identification algorithm is used to determine the fault type of sludge bulking, which is specifically as follows:

① the test samples is used as the input of the type-2 fuzzy-neural-network, and the sludge volume index (SVI) is calculated;

② if SVI≤150, it is determined that there is no sludge bulking during the wastewater treatment process;

③ if SVI>150, sludge bulking at the wastewater treatment operation was determined and regression coefficients of all variables were calculated:

$$b_i(t) = \frac{u_i(t)^T t_i(t)}{t_i(t)^T t_i(t)}, \tag{15}$$

where $b_i(t)$ is the regression coefficient of ith input at time t, $b(t)=[b_1(t), \ldots, b_i(t), \ldots, b_5(t)]$ is the regression coefficient vector, $u_i(t)$ is the ith score vector of the output vector at time t, $U(t)=[u_1(t), \ldots, u_i(t), \ldots, u_5(t)]$ is score matrix of the output vector at time t, $t_i(t)$ is the ith score vector of the input matrix at time t, $T(t)=[t_1(t), \ldots, t_i(t), \ldots, t_5(t)]$ is score matrix of the input matrix at time t, $u_i(t)$ and $t_i(t)$ are given as $$u_i(t) = \frac{y(t)q_i(t)}{q_i(t)^T q_i(t)}, \tag{16}$$

$$t_i(t) = \frac{X(t)w_i(t)}{w_i(t)^T w_i(t)}, \tag{17}$$

where $q_i(t)$ is the ith loading value of output vector at time t, $q(t)\in R^{1\times 5}$ is the loading vector of output vector at time t, $y(t)=[y(t-K+1), y(t-K+2), \ldots, y(t)]^T$, y(t) is the SVI value at time t, $X(t)=[x_1(t), \ldots, x_i(t), \ldots, x_5(t)]$ is the input matrix of type-2 fuzzy-neural-network, $x_i(t)=[x_i(t-K+1), x_i(t-K+2), \ldots, x_i(t)]^T$, $x_i(t)$ is the ith input variable at time t, $w_i(t)$ is the ith feature vector at time t, $W(t)=[w_1(t), \ldots, w_i(t), \ldots, w_5(t)]$ is the feature matrix of $X(t)^T y(t)$, the expressions of $q_i(t)$ and W(t) are $$q_i(t)^T = \frac{t_i(t)^T y(t)}{t_i(t)^T t_i(t)}, \tag{18}$$

$$W(t)^T \Lambda(t) W(t) = E\{X(t)^T y(t) y(t)^T X(t)\}, \tag{19}$$

where $\Lambda(t)$ is the eigenvalue matrices of $X(t)^T y(t)$. The function E represents the eigenvector and eigenvalue of the matrix, the inner relative model of y(t) and X(t) can be expressed as:

$$\begin{cases} X(t) = T(t)P(t)^T + \Delta(t) = \sum_{i=1}^{5} t_i(t)p_i(t)^T + \Delta(t) \\ y(t) = U(t)q(t)^T + G(t) = \sum_{i=1}^{5} u_i(t)q_i(t)^T + G(t) \end{cases}, \tag{20}$$

where $\Delta(t)\in R^{K\times 5}$ is the residual matrix of X(t), $\Delta(t)=[\delta_1(t), \ldots, \delta_i(t), \ldots, \delta_5(t)]$, where $\delta_i(t)$ present the residual vector of ith input. $G(t)\in R^{K\times 1}$ is the residual vector of y(t);

④ when the regression coefficient of the input variable satisfies:

$$b_{max}(t)=\max b(t), \tag{21}$$

where $b_{max}(t)$ is the maximum regression coefficient of the input variables, and the corresponding fault type is the source of sludge bulking.

Figure 4:
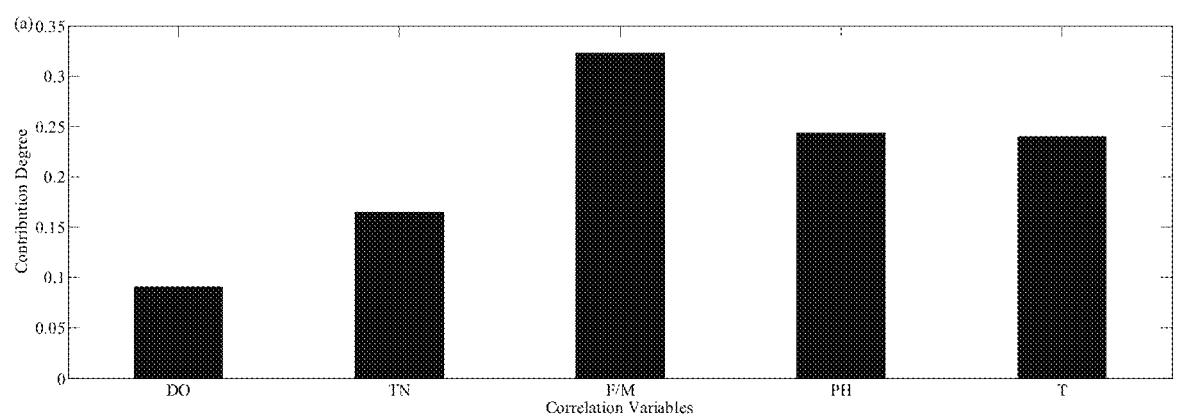
FIG. 4 is the fault category identification diagram of the sludge bulking.

FIG. 4 shows the fault classification of sludge bulking. X-axis: input variable, no unit, Y-axis: contribution, no unit.

What is claimed is:

1. An intelligent identification method for sludge bulking based on a type-2 fuzzy-neural-network, comprising the following steps:
   (1) determine input and output variables of sludge volume index (SVI): in an activated sludge wastewater treatment process, the input variables of SVI soft-computing model include: dissolved oxygen (DO) concentration, total nitrogen (TN) concentration, organic load rate (F/M), pH, T, output values of the soft-computing model are SVI values, the sludge bulking contains the following fault types: low DO concentration, nutrient deficit, low sludge loading, low pH, and low temperature;
   (2) SVI soft-computing model: establish the SVI soft-computing model based on type-2 fuzzy-neural-network, a structure of type-2 fuzzy-neural-network contains five layers: input layer, membership function layer, firing layer, consequent layer and output layer, the network is 5-M-L-2-1, including 5 neurons in the input layer, M neurons in the membership function layer, L neurons in the firing layer, 2 neurons in the consequent layer and 1 neurons in the output layer, M and L are integers larger than 2; connecting weights between the input layer and the membership function layer are assigned 1; the number of training samples is N, the input of type-2 fuzzy-neural-network is $x(t)=[x_1(t), x_2(t), x_3(t), x_4(t), x_5(t)]$ at time t, $x_1(t)$ represents DO concentration at time t; $x_2(t)$ represents TN concentration at time t, $x_3(t)$ represents an organic load rate (F/M) value at time t, $x_4(t)$ represents pH value at time t, and $x_5(t)$ represents T value at time t, the output of type-2 fuzzy-neural-network is $y_d(t)$ and an actual output is y(t); type-2 fuzzy-neural-network includes:

an input layer: there are 5 neurons in this layer, the output is:

$$o_i(t)=x_i(t) \quad (1)$$

where $o_i(t)$ is the ith output value at time t, i=1, 2, . . . , 5, a membership function layer: there are M neurons in the membership function layer, the output is:

$$\tau_m^i(t) = N(c_m^i(t), \sigma_m^i(t); o_i(t)) = \exp\left\{-\frac{1}{2}\left(\frac{o_i(t)-c_m^i(t)}{\sigma_m^i(t)}\right)^2\right\}, \quad (2)$$

$$i = 1, 2, \ldots, 5; m = 1, 2, \ldots, M,$$

$$c_m^i(t) \in [\underline{c}_m^i(t), \overline{c}_m^i(t)], \quad (3)$$

where $\tau_m^i(t)$ is the mth membership function with the ith input at time t, N represents the membership function, $c_m^i(t)$ is the uncertain center of the mth membership function neuron with the ith input at time t, $\underline{c}_m^i(t)$ is the lower center value of the mth membership function neuron with the ith input at time t, $\overline{c}_m^i(t)$ is the upper center value of the mth membership function neuron with the ith input at time t (where the initial lower center value and initial upper center value of the mth membership function neuron with the ith input, i.e., $\underline{c}_m^i(0)$ and $\overline{c}_m^i(t)$ is obtained by that random initial center of the mth membership function neuron with the ith input $c_m^i(0)$ add and subtract a constant), $\sigma_m^i(t)$ is the standard deviation of the mth membership function neuron with the ith input at time t, the bounded internal of $\tau_m^i(t)$ is $[\underline{\tau}_m^i(t), \overline{\tau}_m^i(t)]$ $$\underline{\tau}_m^i(o_i(t)) = \begin{cases} N(\overline{c}_m^i(t), \sigma_m^i(t); o_i(t)), & o_i(t) \leq (\underline{c}_m^i(t)+\overline{c}_m^i(t))/2 \\ N(\underline{c}_m^i(t), \sigma_m^i(t); o_i(t)), & o_i(t) > (\underline{c}_m^i(t)+\overline{c}_m^i(t))/2 \end{cases}, \quad (4)$$

$$\overline{\tau}_m^i(o,(t)) = \begin{cases} N(\underline{c}_m^i(t), \sigma_m^i(t); o_i(t)), & o_i(t) \leq \underline{c}_m^i(t) \\ 1, & \underline{c}_m^i(t) < o_i(t) < \overline{c}_m^i(t) \\ N(\overline{c}_m^i(t), \sigma_m^i(t); o_i(t)), & o_i(t) > \overline{c}_m^i(t) \end{cases}, \quad (5)$$

where $\underline{\tau}_m^i(t)$ and $\overline{\tau}_m^i(t)$ are the lower value and upper value of the mth membership function neuron with the ith input at time t, respectively, $0 < \underline{\tau}_m^i(t) \leq \overline{\tau}_m^i(t) \leq 1$, a firing layer: there are L neurons in this layer, and the output values are:

$$F_l(t) = [\underline{f}_l(t), \overline{f}_l(t)], \underline{f}_l(t) = \prod_{i=1}^{5} \underline{\tau}_m^i(t), \overline{f}_l(t) = \prod_{i=1}^{5} \overline{\tau}_m^i(t), \quad (6)$$

$$l = 1, 2, \ldots, L,$$

where $F_l(t)$ is the firing strength of the lth firing neuron, $\underline{f}_l(t)$ and $\overline{f}_l(t)$ are the lower firing strength and upper firing strength of the lth firing neuron, respectively, $0 < \underline{f}_l(t) \leq \overline{f}_l(t) \leq 1$, a consequent layer: this layer contains two consequent neurons, the output values are $$\underline{y}(t) = \frac{\sum_{l=1}^{L} \underline{f}_l(t) a_l(t)}{\sum_{l=1}^{L} \underline{f}_l(t)}, \overline{y}(t) = \frac{\sum_{l=1}^{L} \overline{f}_l(t) a_l(t)}{\sum_{l=1}^{L} \overline{f}_l(t)}, a_l(t) = \sum_{i=1}^{5} \theta_l^i(t) x_i(t), \quad (7)$$

where $\underline{y}(t)$ and $\overline{y}(t)$ are the low and up output values of the consequent neurons, $a_l(t)$ is weight of the lth firing neuron, $\theta_l^i(t)$ is the weight coefficient of the lth firing neuron with the ith input at time t, an output layer: the output value is:

$$y(t)=\eta(t)\underline{y}(t)+(1-\eta(t))\overline{y}(t) \quad (8)$$

where $\eta(t)$ and y(t) are the proportion of the low output and the output value of type-2 fuzzy-neural-network, the error of type-2 fuzzy-neural-network is:

$$E(t) = \frac{1}{N}\sum_{t=1}^{N}(y_d(t)-y(t))^2 \quad (9)$$

where $y_d(t)$ is the output of type-2 fuzzy-neural-network and the actual output is expressed as y(t);

(3) train type-2 fuzzy-neural-network (a) give the type-2 fuzzy-neural-network, the initial number of firing layer neurons is M, M>2 is a positive integer; the input of type-2 fuzzy-neural-network is x(1), x(2), . . . , x(t), . . . , x(N), correspondingly, the output is $y_d(1), y_d(2), \ldots, y_d(t), \ldots, y_d(N)$, expected error value is set to $E_d$, $E_d \in (0, 0.01)$, (b) set the learning step s=1;

(c) t=s; according to Eqs. (1)-(7), calculate the output of type-2 fuzzy-neural-network, exploiting adaptive second-order algorithm:

$$\psi(t+1)=\psi(t)+(H(t)+\lambda(t)I)^{-1}v(t) \quad (10)$$

where $\psi(t)=[\underline{c}_m^i(t), \overline{c}_m^i(t), \sigma_m^i(t), \eta(t), w_m^i(t)]$ is the parameter matrix of type-2 fuzzy-neural-network at time t, $\underline{c}_m^i(t)$ is the lower center value of the mth membership function neuron with the ith input at time t, $\overline{c}_m^i(t)$ is the upper center value of the membership function neuron with the ith input at time t, $\sigma_m^i(t)$ is the standard deviation of the mth membership function neuron with the ith input at time t, $\eta(t)$ is the proportion of the lower output, $\theta_l^i(t)$ is the weight coefficient of the lth firing neuron with the ith input at time t, H(t) is the quasi Hessian matrix, v(t) is gradient vector, I is the identity matrix and $\lambda(t)$ is the adaptive learning rate defined as:

$$\lambda(t)=\gamma|E(t)|+(1-\gamma)\|v(t)\| \quad (11)$$

where $\gamma \in (0, 1)$, the expression of H(t) and v(t) are defined as:

$$H(t)=J^T(t)J(t) \quad (12)$$

$$v(t)=J^T(t)E(t) \quad (13)$$

where the Jacobian vector J(t) is calculated as:

$$J(t) = \left[\frac{\partial e(t)}{\partial c_m^i(t)}, \frac{\partial e(t)}{\partial \bar{c}_m^i(t)}, \frac{\partial e(t)}{\partial \sigma_m^i(t)}, \frac{\partial e(t)}{\partial \eta(t)}, \frac{\partial e(t)}{\partial \theta_m^i(t)}\right] \quad (14)$$

(d) according to Eq. (9), calculate the performance of type-2 fuzzy-neural-network, if $E(t) \geq E_d$, go to step (c); if $E(t) < E_d$, stop the training process;

(4) the target-related identification algorithm is used to determine the fault type of sludge bulking, which is specifically as follows:

(a) the test samples are used as the input of the type-2 fuzzy-neural-network, and the sludge volume index (SVI) is calculated;

(b) if SVI≤150, it is determined that there is no sludge bulking during the wastewater treatment process;

(c) if SVI>150, sludge bulking at the wastewater treatment operation is determined and regression coefficients of all variables are calculated:

$$b_i(t) = \frac{u_i(t)^T t_i(t)}{t_i(t)^T t_i(t)}, \quad (15)$$

where $b_i(t)$ is the regression coefficient of ith input at time t, $b(t)=[b_1(t), \ldots, b_i(t), \ldots, b_5(t)]$ is the regression coefficient vector, $u_i(t)$ is the ith score vector of the output vector at time t, $U(t)=[u_1(t), \ldots, u_i(t), \ldots, u_5(t)]$ is score matrix of the output vector at time t, $t_i(t)$ is the ith score vector of the input matrix at time t, $T(t)=[t_1(t), \ldots, t_i(t), \ldots, t_5(t)]$ is score matrix of the input matrix at time t, $u_i(t)$ and $t_i(t)$ are given as:

$$u_i(t) = \frac{y(t) q_i(t)}{q_i(t)^T q_i(t)}, \quad (16)$$

$$t_i(t) = \frac{X(t) w_i(t)}{w_i(t)^T w_i(t)}, \quad (17)$$

where $q_i(t)$ is the ith loading value of output vector at time t, $q(t) \in R^{1 \times 5}$ is the loading vector of output vector at time t, $y(t)=[y(t-K+1), y(t-K+2), \ldots, y(t)]^T$, $y(t)$ is the SVI value at time t, $X(t)=[x_1(t), \ldots, x_i(t), \ldots, x_5(t)]$ is the input matrix of type-2 fuzzy-neural-network, $x_i(t)=[x_i(t-K+1), x_i(t-K+2), \ldots, x_i(t)]^T$, $x_i(t)$ is the ith input variable at time t, $w_i(t)$ is the ith feature vector at time t, $W(t)=[w_1(t), \ldots, w_i(t), \ldots, w_5(t)]$ is the feature matrix of $X(t)^T y(t)$, the expressions of $q_i(t)$ and $W(t)$ are $$q_i(t)^T = \frac{t_i(t)^T y(t)}{t_i(t)^T t_i(t)}, \quad (18)$$

$$W(t)^T \Lambda(t) W(t) = E\{X(t)^T y(t) y(t)^T X(t)\}, \quad (19)$$

where $\Lambda(t)$ is the eigenvalue matrices of $X(t)^T y(t)$, the function E represents the eigenvector and eigenvalue of the matrix, the inner relative model of y(t) and X(t) can be expressed as:

$$\begin{cases} X(t) = T(t) P(t)^T + \Delta(t) = \sum_{i=1}^{5} t_i(t) p_i(t)^T + \Delta(t) \\ y(t) = U(t) q(t)^T + G(t) = \sum_{i=1}^{5} u_i(t) q_i(t)^T + G(t) \end{cases}, \quad (20)$$

where $\Delta(t) \in R^{K \times 5}$ is the residual matrix of X(t), $\Delta(t)=[\delta_1(t), \ldots, \delta_i(t), \ldots, \delta_5(t)]$, where $\delta_i(t)$ present the residual vector of ith input, $G(t) \in R^{K \times 1}$ is the residual vector of y(t);

(d) when the regression coefficient of the input variable satisfies:

$$b_{max}(t) = \max b(t), \quad (21)$$

where $b_{max}(t)$ is the maximum regression coefficient of the input variables, and the corresponding fault type is the source of sludge bulking.

\* \* \* \* \*